United States Patent [19]

Pescatore

[11] 4,456,001

[45] Jun. 26, 1984

[54] APPARATUS FOR EQUINE HOOF TREATMENT

[75] Inventor: Eugene A. Pescatore, Elmwood Park, N.J.

[73] Assignee: Electro-Biology, Inc., Fairfield, N.J.

[21] Appl. No.: 394,691

[22] Filed: Jul. 2, 1982

[51] Int. Cl.³ ............................................. A61N 1/40
[52] U.S. Cl. .................................. 128/1.5; 128/82.1; 128/419 F; 128/795; 128/802
[58] Field of Search ....................... 128/1.3, 1.5, 82.1, 128/419 F, 783, 798, 802, 795

[56] References Cited

U.S. PATENT DOCUMENTS 4,240,437 12/1980 Church ........................... 128/420 R
4,266,532 5/1981 Ryaby et al. .................... 128/802 X

FOREIGN PATENT DOCUMENTS 2618947 11/1976 Fed. Rep. of Germany ...... 128/795

Primary Examiner—Lee S. Cohen
Attorney, Agent, or Firm—Hopgood, Calimafde, Kalil, Blaustein & Judlowe

[57] ABSTRACT

The invention contemplates a boot removably adapted for attachment to an engine hoof and carrying at least one multi-turn electrical coil which effectively surrounds at least the bottom of the hoof. A pulse generator and power source are self-contained in a housing carried at the back side of the boot, with provision for electrically exciting the coil with a succession of therapeutically beneficial low-voltage unidirectional asymmetrical pulses.

10 Claims, 5 Drawing Figures

4,456,001

APPARATUS FOR EQUINE HOOF TREATMENT

BACKGROUND OF THE INVENTION

The invention relates to an electromagnetic body-treatment device for surgically non-invasive modification of the growth repair and maintenance behavior of living tissues and/or cells within an equine or the like hoof, by a specific and selective change in electrical environment.

Applicable background is discussed at length in Ryaby, et al., U.S. Pat. No. 4,105,017 and in various patents having a continuation-in-part relation thereto. Reference is therefore made to said patents for background discussion. It suffices to note that, although said patents speak generally in the context of controlled modification of cellular and/or tissue growth, the primary emphasis on osteogenic applications to human beins, was initially limited to such "hopeless" cases as pseudarthroses and other non-unions.

The application of pulsed electromagnetic fields of the character indicated is being extended to veterinary applications, where impressive results are being achieved in aid of rapid recovery by horses, particularly race horses, from the kinds of bone and bone-related injury variously known as saucer fractures, damaged suspensories, splints and bucks. It is not infrequent that the third phalanges bone, within the hoof, will suffer fracture, but this region is not available for treatment with prior coil configurations, and a horse will not willingly permit attempted treatment with a device which can be kicked or destroyed or which requires connection to an external source of power.

BRIEF STATEMENT OF THE INVENTION

It is an object of the invention to provide improved applicator means, removably adapted for the pulsed electromagnetically stimulated treatment of hoof-related injury of the character indicated.

It is a specific object to provide a completely self-contained device of the character indicated which can be applied to an injured hoof, which is of negligible weight and inconvenience to the animal and which may therefore be left in place on the hoof for prolonged periods, with selective availability of control of treatment intervals in relation to nontreatment intervals within a given day.

The invention achieves the foregoing objects by employing attachment structure in the form of a boot of non-conductive magnetically transparent material which may be a unitary combination of a relatively stiff sole portion with a relatively flexible upper portion. Various embodiments are disclosed for coil configurations which can develop therapeutically beneficial magnetic-flux distribution in the hoof, in conjunction with self-contained light-weight pulse-signal generator means for coil excitation. The signal-generator means is contained in a housing comparable to the size of a cigarette package, carried by the upper portion and at the backside of the hoof.

DETAILED DESCRIPTION

The invention will be described for three illustrative embodiments, in conjunction with the accompanying drawings, in which.

Figure 1:
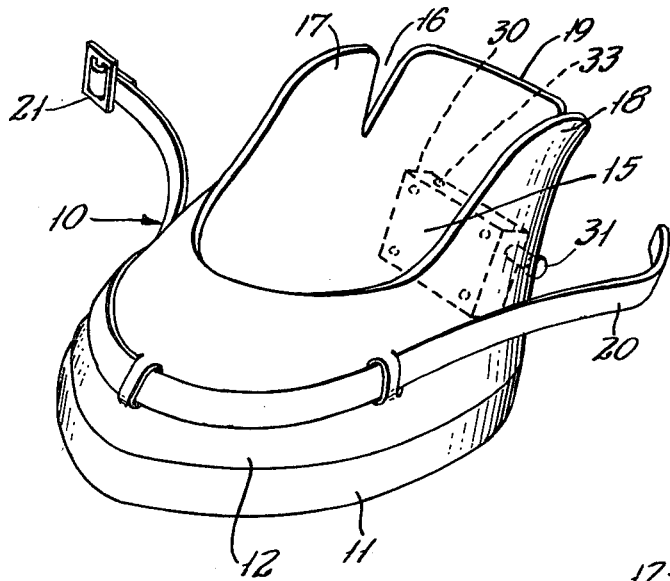
FIG. 1 is a front three-quarter perspective view of a first embodiment of the invention.

All three embodiments may be built into or upon a boot 10 having the general appearance depicted in FIG. 1. Commercial hoof boots are available from various manufacturers, including Barrier Corporation, Mineral Wells, Tex.; they are commercially offered to protect and cushion conventionally shod hoofs for durability in rough-riding races over rough terrain. Such boots are of one-piece molded vinyl construction and come in a range of sizes, to assure correct fit to the particular shod horse. However, in the context of the present invention, the conventional iron shoe is removed and is preferably replaced by an all-plastic shoe, for example to give stability to a fractured third phalanges bone to be treated. Hoof-boot size should therefore be selected in the context of the afflicted hoof size when fitted with the plastic horseshoe.

As shown, the commercial hoof boot 10 comprises a relatively stiff sole portion 11 integrally connected at its periphery with a relatively flexible upper portion 12. The interior volume within the upper portion 12 will be understood to be suited for conformance to the particular hoof to be treated. The bottom of the sole portion 11 is characterized by an integrally formed downward projection 13 in the shape of the horse's shoe, conventionally iron, but here understood to be preferably a plastic shoe to stabilize bone fragments. The integral projection 13 will be understood to fully register with the horse's shoe, for optimum distribution of leg-bearing forces at ground contact. The region 14 within projection 13 is offset from ground contact. The profile of the upper portion 12 rises toward the backside 15 of boot 10, and rear corners are slit, as at 16, to define opposed side tabs 17–18 and a rear tab 19 for finger engagement, as an aid in applying the boot to the hoof. A belt 20, threaded through spaced pairs of apertures in upper portion 12, completes the commercially available boot, being provided with suitable means 21 at one end for releasably cinched circumferential belt retention of the upper portion 12 to hoof contour.

Figure 2:
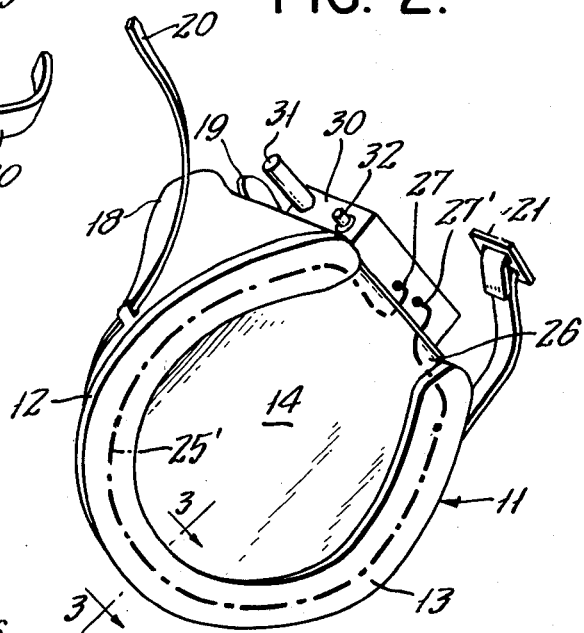
FIG. 2 is another three-quarter perspective view of the device of FIG. 1, as viewed from below.
Figure 3:
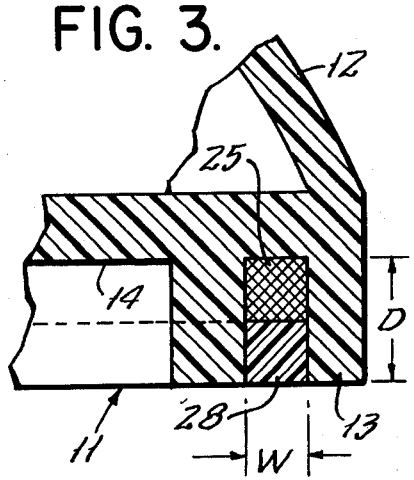
FIG. 3 is an enlarged fragmentary vertical sectional view taken at 3—3 of FIG. 2.

In the form of FIGS. 1 to 3, the horseshoe-shaped projection 13 has been routed along its median contour to define a channel of depth D and width W, to accommodate insertion of a multi-turn electrical coil 25; the depth D may suitably coincide with the recessed extent of the sole region 14. The thus-inserted contour of coil 25 has been indicated by a heavy phantom course 25' in FIG. 2, leaving a rear segment of the coil exposed at the region 26 of sole 14, between the spaced rear ends of the horseshoe shape of projection 13. The coil 25 is so oriented in its insertion within the routed groove that coil leads 27–27' are available in the rear sole region 26. Coil placement is rendered into a permanent embedment by suitable potting 28 (FIG. 3) in the routed groove, and the potting material is preferably further applied over exposed coil and lead segments at the rear sole region.

A generally prismatic signal-generator housing 30 is securely fastened to the back 15 of the upper portion 12. Housing 30 will be understood to contain a power source, such as a rechargeable battery and pulse-generator means, the latter being generally as described in said Ryaby, et al. patent, and output of the pulse generator being directly connected to leads 27—27'. As shown, a removable plus 31 provides access for the output jack of conventional battery-charging means (not shown). Also, as shown, an externally accessible push-button switch 32 enables an operator to switch the signal generator from inactive to active state, and vice versa, for intermittent periods of time, as for example, one or more two-hour treatment periods as may be prescribed for each day. Further, as shown, a small indicator lamp 33 will be understood to be viewable at the top edge of housing 30, to show to the operator whether the pulse generator is or is not in operation.

To apply the boot of FIGS. 1 to 3 to an afflicted hoof, it is of course first necessary to remove the horse's conventional iron shoe, preferably replacing the same with a magnetically transparent (plastic) shoe. The hoof is then inserted, and prompt and properly seated fit is aided by grasping one or more of the upper tab regions 17-18-19. The belt 20 is then fastened behind back panel 15.

Figure 4:
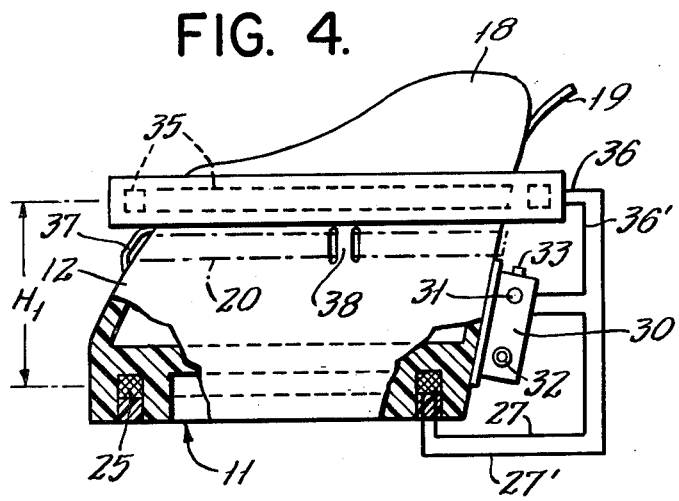
FIG. 4 is a view in side elevation of a second embodiment, with portions broken-away and in section to reveal internal detail.

The modification of FIG. 4 differs from that of FIGS. 1 to 3, in that an additional multi-turn electrical coil 35 is mounted to the upper portion 12, and its leads 36—36' are so connected to the output of signal generator means 30 as to be in flux-aiding relation to the concurrently excited lower coil 25. Such excitation connections to coils 25-35 may be in parallel, but their preferred series connection is schematically indicated.

As shown, the upper coil 35 is a separate assembly, preferably an annular potted embedment of coil 35 in yieldable protective plastic, wherein the separate assembly integrally includes dependent flange formations as at tabs 37-38, each of which may have a pair of slots for threaded reception of belt 20. For simplicity, the alignment of belt 20 is shown only by phantom outline in FIG. 4, and it will be understood that by having the slots of tabs 37-38 in substantial register with the slot pairs in upper portion 12, a threading of belt 20 via registering slots will provide anchorage and support of the second coil 35, once belt 20 is fastened.

To apply the structure of FIG. 4 to an afflicted hoof, the procedure described for FIGS. 1 to 3 is repeated, except that, before inserting the hoof into boot 10, the upper coil (35) assembly is maneuvered around the hoof and to a raised position, say to the region of first or second phalanges bones, the boot 10 being then applied, followed by lowered positioning of the coil (35) assembly, in overlap with the upper portion 12 and with tabs 37-38 suitably positioned for belt (20) threading. Such maneuvering of the coil (35) assembly is aided by the indicated flexible nature of associated potting, and it is also aided by providing removable jack or the like electrical connection for leads 36—36'. The completed assembly to the hoof results in coils 25-35 being supported at substantially parallel horizontal planes wherein the effective spacing $H_1$ between horizontal planes is less than the mean effective diameter of the coils.

Figure 5:
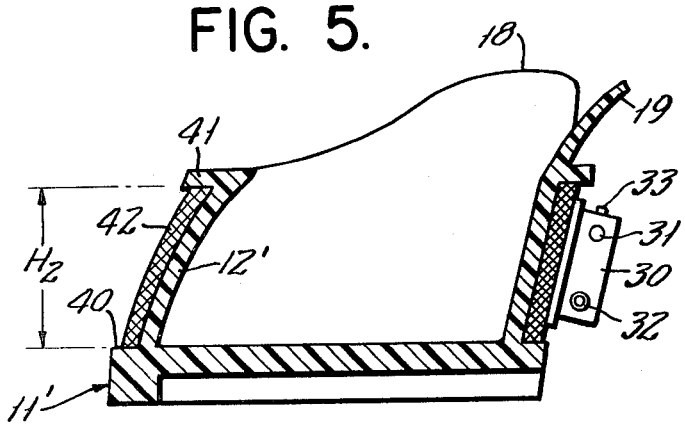
FIG. 5 is a vertical sectional view to show a third embodiment.

In the embodiment of FIG. 5, the basic boot structure is generally as already described, except that the sole portion 11' features a short peripheral retaining ledge 40, and the upper portion 12' features similar ledge means 41 at spacing $H_2$ above ledge 40. The ledge means 41 may comprise a plurality of peripherally spaced lugs, thus permitting use of rear-corner slits (as at 16, in FIG. 1), to define tabs 17-18-19, for ease of boot application. The further structure of FIG. 5 is a separate assembly, being a single multi-turn electrical coil 42 which may be a helical development of spaced turns, embedded for convenience in yieldable potting plastic into the form of a continuous flexible belt, of contour adapted for ultimate conformation to the upper boot portion 12'; potted coil 42 will be understood to include a suitably shaped back panel region to which self-contained battery and pulse-generator means 30 is secured, with electrical-output connection to coil 42.

To apply the FIG. 5 structure to an afflicted hoof, preferably re-shod with a magnetically transparent shoe, the flexible coil (42) belt is first manipulated over the hoof and then elevated, as in the case of the coil (35) assembly of FIG. 4. The boot is then fitted to the hoof, and thereafter the flexible coil belt 42 is manipulated over the ledge or lug means 41, being self-retaining between ledges 40-41 and being also an effective replacement of belt 20 when thus positioned.

The Ryaby, et al. patents referred to above describe value ranges for various parameters of applied signals. Generally, the signals found effective for equine treatment involve energy and frequency levels at or below lower limits of ranges specified by Ryaby, et al. Specifically, for equine applicators of the type herein described, it is found effective to provide asymmetrical pulse excitation of the described coil or coils. The pulses are of quasi-rectangular form, comprising a first pulse portion of relatively low-magnitude first polarity and of approximately 250 microsecond duration, followed by a second pulse portion of relatively great-magnitude second polarity and of approximately 5 microsecond duration. Such pulses are repeated in bursts of 50 milliseconds, i.e., at about 4 kHz, and the bursts are repeated at a repetition rate of 2 Hz. The amplitude of excitation signal is such as to develop a maximum body-induced voltage of approximately 0.15 millivolt per centimeter of treated tissue and/or cells, as measured by a one-cm diameter probe coil of the type described in said Ryaby, et al. patent. Stated more generally, present experience indicates that the burst-repetition rate should be in the range of 1 to 5 Hz, that the pulses within each burst should be in the range of 2 to 5 kHz, and that the burst duration should be approximately one tenth the period of burst repetition. The involved maximum magnetic-field strength is approximately 2 Gauss. For the single-coil configurations of FIGS. 1 to 3 and 5, coil 25 (42) may suitably comprise 40 turns of 24 AWG enameled copper wire, to a nominal diameter of about 4.5 inches; for the series-connected two-coil configuration of FIG. 4, each of coils 25 and 35 may suitably comprise 25 turns of 22 AWG enameled copper wire, to the same nominal diameter.

While the invention has been described in detail for illustrative embodiments, it will be understood that modifications may be made without departing from the invention. For example, the routing described in connection with FIG. 3, in connection with coil embedment in the sole portion 11, is to be understood as purely illustrative, in that a boot 10 can be molded with coil 25 in place, thus providing an integrally formed structure which includes the coil; alternatively, the coil may be a part of a pad or lining insert suitable for nesting within the boot cavity and resting on or adhered to the sole portion 11.

What is claimed is:

1. An electromagnetic body-treatment device for surgically non-invasive modification of the growth repair and maintenance behavior of living tissues and/or cells within an equine hoof by a specific and selective change in electrical environment, comprising a boot of magnetically transparent material and having a relatively stiff sole portion and a relatively flexible upper portion peripherally connected to the sole portion, the upper portion being shaped for removable conforming application to hoof side contour, the bottom of said sole portion being characterized by an integral downward projection of horseshoe shape and with a multi-turn electrical coil embedded in the horseshoe region of said sole portion, the turns of said coil being generally in the horizontal plane of said sole portion and defining a magnetically transparent included area in substantial conformance with that of the bottom area of the hoof, whereby said coil is poised to establish an upstanding axis of symmetry of magnetic-flux concentration in the hoof, and self-contained means carried by said boot and connected to said coil for electrically exciting said coil with a succession of low-voltage unidirectional asymmetrical pulses.

2. The treatment device of claim 1, in which said coil is one of two, the second coil being of size to accommodate hoof insertion and being carried by the upper portion of said boot in a substantially horizontal plane, said second coil being electrically connected to said self-contained means and in flux-aiding relation to flux development attributable to said first-mentioned coil.

3. The treatment device of claim 2, in which said coils are series-connected to said last-defined means.

4. The treatment device of claim 2, in which said second coil is detachably connected to said upper portion and is detachably connected to said last-defined means.

5. The treatment device of claim 4, in which said second coil includes magnetically transparent mounting means, and in which a circumferential strap is threaded through locating apertures in said upper portion and in said mounting means to retain the connected relation of said second coil with said upper portion.

6. An electromagnetic body-treatment device for surgically non-invasive modification of the growth repair and maintenance behavior of living tissues and/or cells within an equine hoof by a specific and selective change in electrical environment, comprising a boot of magnetically transparent material and having a relatively stiff sole portion and a relatively flexible upper portion peripherally connected to the sole portion, the upper portion being shaped for removable conforming application to hoof side contour, a single multi-turn electrical coil carried by said upper portion, the turns of said coil conforming generally to the outer contour of said upper portion and being in vertically spaced progression to substantially the vertical extent of said upper portion, and self-contained means carried by said boot and connected to said coil for electrically exciting said coil with a succession of low-voltage unidirectional asymmetrical pulses.

7. The treatment device of claim 1 or claim 2 or claim 6, in which said pulses are in bursts at a burst-repetition rate in the range of one to 5 Hz, wherein pulses within each burst are in the repetition-rate range of 2 to 5 kHz, and wherein burst duration is approximately one tenth the period of burst repetition.

8. The treatment device of claim 1 or claim 2 or claim 6, in which said pulses are in bursts at a burst-repetition rate of about 2 Hz, wherein pulses within each burst are at a repetition rate of 3 to 4 kHz, and wherein burst duration is approximately one tenth the period of burst repetition.

9. The treatment device of claim 1 or claim 2 or claim 6, in which said boot is a single molded product of plastic material.

10. The treatment device of claim 1 or claim 2 or claim 6, in which said last-defined means includes a housing mounted to the back side of said upper portion and contains a source of electric power, an externally accessible switch for on-off control of said excitation, and an externally viewable indicator of operational state.

* * * * *